(12) United States Patent
Daley et al.

(10) Patent No.: US 10,626,089 B2
(45) Date of Patent: Apr. 21, 2020

(54) QUINOLINE DERIVATIVE IN CRYSTAL FORM

(71) Applicant: GB001, Inc., San Diego, CA (US)

(72) Inventors: Donald John Daley, Bishops Stortford (GB); John Gary Montana, Ashdon (GB); George Hynd, Epping (GB); Mitsuru Teramoto, Chiyoda-ku (JP); Takahiro Ito, Honjo (JP)

(73) Assignee: GBOO1, Inc., San Diego, CA (US)

( * ) Notice: Subject to any disclaimer, the term of this patent is extended or adjusted under 35 U.S.C. 154(b) by 0 days.

(21) Appl. No.: 16/522,323

(22) Filed: Jul. 25, 2019

(65) Prior Publication Data

US 2020/0017447 A1    Jan. 16, 2020

Related U.S. Application Data

(63) Continuation of application No. 16/302,553, filed as application No. PCT/JP2017/018165 on May 15, 2017.

(30) Foreign Application Priority Data

May 16, 2016   (JP) .................................. 2016-097872

(51) Int. Cl.
    *C07D 215/22*    (2006.01)
(52) U.S. Cl.
    CPC ........ *C07D 215/22* (2013.01); *C07B 2200/13* (2013.01)
(58) Field of Classification Search
    CPC ............................................... C07D 215/233
    USPC ....................................................... 546/153
    See application file for complete search history.

(56) References Cited

U.S. PATENT DOCUMENTS 7,858,640 B2 * 12/2010 Cramp .................. A61K 31/47
                                                      514/311

FOREIGN PATENT DOCUMENTS

| JP | 49-25118 | 3/1974 |
| JP | 49-100212 | 9/1974 |
| JP | 2-160758 A | 6/1990 |
| JP | 2009-19030 A | 1/2009 |
| JP | 2009-514797 A | 4/2009 |
| JP | 2011-168587 A | 9/2011 |
| JP | 2012-533570 A | 12/2012 |
| JP | 2013-522232 A | 6/2013 |
| WO | 2007/036743 A2 | 4/2007 |

OTHER PUBLICATIONS

Bastin et al., "Salt Selection and Optimisation Procedures for Pharmaceutical New Chemical Entities," Organic Process Research and Development, vol. 4, No. 5, 2000.
edited by Noriaki Hirayama, Yuki Kagobutsu Kessho Sakusei Handbook—Genri to Know-how-, Maruzen Co., Ltd., Jul. 25, 2008 (Jul. 25, 2008), pp. 57 to 84. (Reference Unavailable).
International Search Report for PCT/JP2017/018165 dated Jun. 27, 2017.

* cited by examiner

*Primary Examiner* — Charanjit Aulakh
(74) *Attorney, Agent, or Firm* — Seed IP Law Group LLP

(57) ABSTRACT

Crystals of [8-chloro-3-(4-chlorobenzyl)-4-difluoromethoxy-2-ethylquinolin-5-yloxy]acetic acid L-lysine salt, i.e., a crystal A which has peaks at diffraction angles 2θ=6.0°, 10.0°, 10.7°, 12.1°, 18.4°, 19.2° and 20.1° in powder X-ray diffraction spectra and a crystal B which has peaks at diffraction angles 2θ=6.0°, 11.7°, 12.4°, 15.2°, 16.4°, 20.3° and 22.6° in powder X-ray diffraction spectra. These crystals are chemically stable and have excellent thermal stability and physical properties, and are therefore suitable as medicinal substances.

17 Claims, 7 Drawing Sheets

QUINOLINE DERIVATIVE IN CRYSTAL FORM

TECHNICAL FIELD

The present invention relates to [8-chloro-3-(4-chlorobenzyl)-4-difluoromethoxy-2-ethylquinolin-5-yloxy]acetic acid L-lysine salt in crystal form.

BACKGROUND TECHNOLOGY

The compound [8-chloro-3-(4-chlorobenzyl)-4-difluoromethoxy-2-ethylquinolin-5-yloxy]acetic acid is described in example 39 of patent citation 1. Patent citation 1 also states that this compound is useful in the treatment and prevention of diseases in which CRTH2 (chemoattractant receptor-homologous molecule expressed on Th2 cells) receptors participate, such as bronchial asthma, chronic obstructive pulmonary disease, allergic airway syndrome, bronchitis, cystic fibrosis, emphysema, rhinitis, etc., and psoriasis, atopic and nonatopic dermatitis, Crohn's disease, ulcerative colitis, and irritable bowel disease, etc.

From that described in patent citation 1 and technical common sense, it can also be understood that this compound is useful in the treatment and prevention of perennial allergic rhinitis, seasonal allergic rhinitis, chronic eosinophilic rhinosinusitis, chronic noneosinophilic rhinosinusitis, chronic spontaneous urticaria, and eosinophilic gastrointestinal disease.

However, patent citation 1 does not mention [8-chloro-3-(4-chlorobenzyl)-4-difluoromethoxy-2-ethylquinolin-5-yloxy]acetic acid or the L-lysine salt thereof in crystal form.

CITATIONS OF THE PRIOR ART

Patent Citations

Patent citation 1: International patent publication WO2007/036743

SUMMARY OF THE INVENTION

Problem to be Solved by the Invention

The aim of the present invention is to provide [8-chloro-3-(4-chlorobenzyl)-4-difluoromethoxy-2-ethylquinolin-5-yloxy]acetic acid in crystal form, that is chemically stable and suitable as a pharmaceutical drug substance.

Means of Solving the Problem

As a result of diligent research into achieving the above-mentioned aim, the present inventors discovered that [8-chloro-3-(4-chlorobenzyl)-4-difluoromethoxy-2-ethylquinolin-5-yloxy]acetic acid L-lysine salt (hereafter also referred to as "compound (I)") can be crystallized, and that it has at least two crystal polymorphs. Also, they arrived at the present invention upon discovering that the resulting crystal form has a higher melting point, better thermal stability and physical properties than the free form of [8-chloro-3-(4-chlorobenzyl)-4-difluoromethoxy-2-ethylquinolin-5-yloxy]acetic acid (hereafter also referred to simply as "free form"; melting point 141° C.) which is not in salt form, and are very useful as a pharmaceutical drug substance.

Specifically, the present invention is:
[1] [8-Chloro-3-(4-chlorobenzyl)-4-difluoromethoxy-2-ethylquinolin-5-yloxy]acetic acid L-lysine salt in crystal form;
[2] [2] the crystal form described in [1], which is crystal form A;
[3] the crystal form described in [1] (crystal form A), which, in its powder X-ray diffraction spectrum, has peaks at diffraction angles 2θ=6.0°, 10.0°, 10.7°, 12.1°, 18.4°, 19.2°, and 20.1°;
[4] the crystal form described in [1] (crystal form A), which has the powder X-ray diffraction spectrum pattern shown in FIG. 1;
[5] the crystal form described in [1] (crystal form A), which, in its infrared absorption spectrum, has peaks at wavenumbers 673 $cm^{-1}$, 810 $cm^{-1}$, 872 $cm^{-1}$, 1010 $cm^{-1}$, 1051 $cm^{-1}$, 1413 $cm^{-1}$, and 1568 $cm^{-1}$;
[6] the crystal form described in [1] (crystal form A), which has the infrared absorption spectrum pattern shown in FIG. 3;
[7] the crystal form described in [1] (crystal form A), which, in its solid-state $^{13}$C-NMR spectrum, has chemical shift peaks at 107.1 ppm, 115.9 ppm, 127.5 ppm, 136.5 ppm, 145.7 ppm, 152.7 ppm, 153.8 ppm, 165.8 ppm, 175.8 ppm, 177.3 ppm, and 179.5 ppm;
[8] the crystal form described in [1] (crystal form A), which has the solid-state $^{13}$C-NMR spectrum pattern shown in FIG. 5;
[9] the crystal form described in [1] (crystal form A), which, in its solid-state $^{19}$F-NMR spectrum, has chemical shift peaks at −77.0 ppm, and −72.3 ppm;
[10] the crystal form described in [1] (crystal form A), which have the solid-state $^{19}$F-NMR spectrum pattern shown in FIG. 6;
[11] the crystal form described in [1] (crystal form A), which, in its solid-state $^{15}$N-NMR spectrum, has a chemical shift peak at −347.2 ppm;
[12] the crystal form described in [1] (crystal form A), which has the solid-state $^{15}$N-NMR spectrum pattern shown in FIG. 7;
[13] the crystal form described in [1], which are crystal form B;
[14] the crystal form described in [1] (crystal form B), which, in its powder X-ray diffraction spectrum, has peaks at diffraction angles 2θ=6.0°, 11.7°, 12.4°, 15.2°, 16.4°, 20.3°, and 22.6°;
[15] the crystal form described in [1] (crystal form B), which has the powder X-ray diffraction spectrum pattern shown in FIG. 2;
[16] the crystal form described in [1] (crystal form B), which, in its infrared absorption spectrum, has peaks at wavenumbers 667 $cm^{-1}$, 803 $cm^{-1}$, 885 $cm^{-1}$, 1012 $cm^{-1}$, 1032 $cm^{-1}$, 1402 $cm^{-1}$, and 1597 $cm^{-1}$;
[17] the crystal form described in [1] (crystal form B), which has the infrared absorption spectrum pattern shown in FIG. 4;
[18] a pharmaceutical composition containing the crystal form described in any of [1]-[17] and pharmaceutically acceptable carrier;
[19] a CRTH2 antagonist containing, as active ingredient, the crystal form described in any of [1]-[17];
[20] a therapeutic drug or preventive drug for one or more diseases chosen from the group consisting of bronchial asthma, chronic obstructive pulmonary disease, bronchitis, cystic fibrosis, perennial allergic rhinitis, seasonal allergic rhinitis, chronic eosinophilic rhinosinusitis, and chronic noneosinophilic rhinosinusitis, containing, as active ingredient, the crystal form described in any of [1]-[17]; and

[21] a therapeutic drug or preventive drug for one or more diseases chosen from the group consisting of psoriasis, atopic and nonatopic dermatitis, chronic spontaneous urticaria, Crohn's disease, ulcerative colitis, eosinophilic gastrointestinal disease, and irritable bowel disease, containing, as active ingredient, the crystal form described in any of [1]-[17].

Advantages of the Invention

The present invention provides [8-chloro-3-(4-chlorobenzyl)-4-difluoromethoxy-2-ethylquinolin-5-yloxy]acetic acid L-lysine salt in crystal form, that is chemically stable, has superior thermal stability and physical properties, and is suitable as a pharmaceutical drug substance.

MODE OF THE INVENTION

Figure 1:
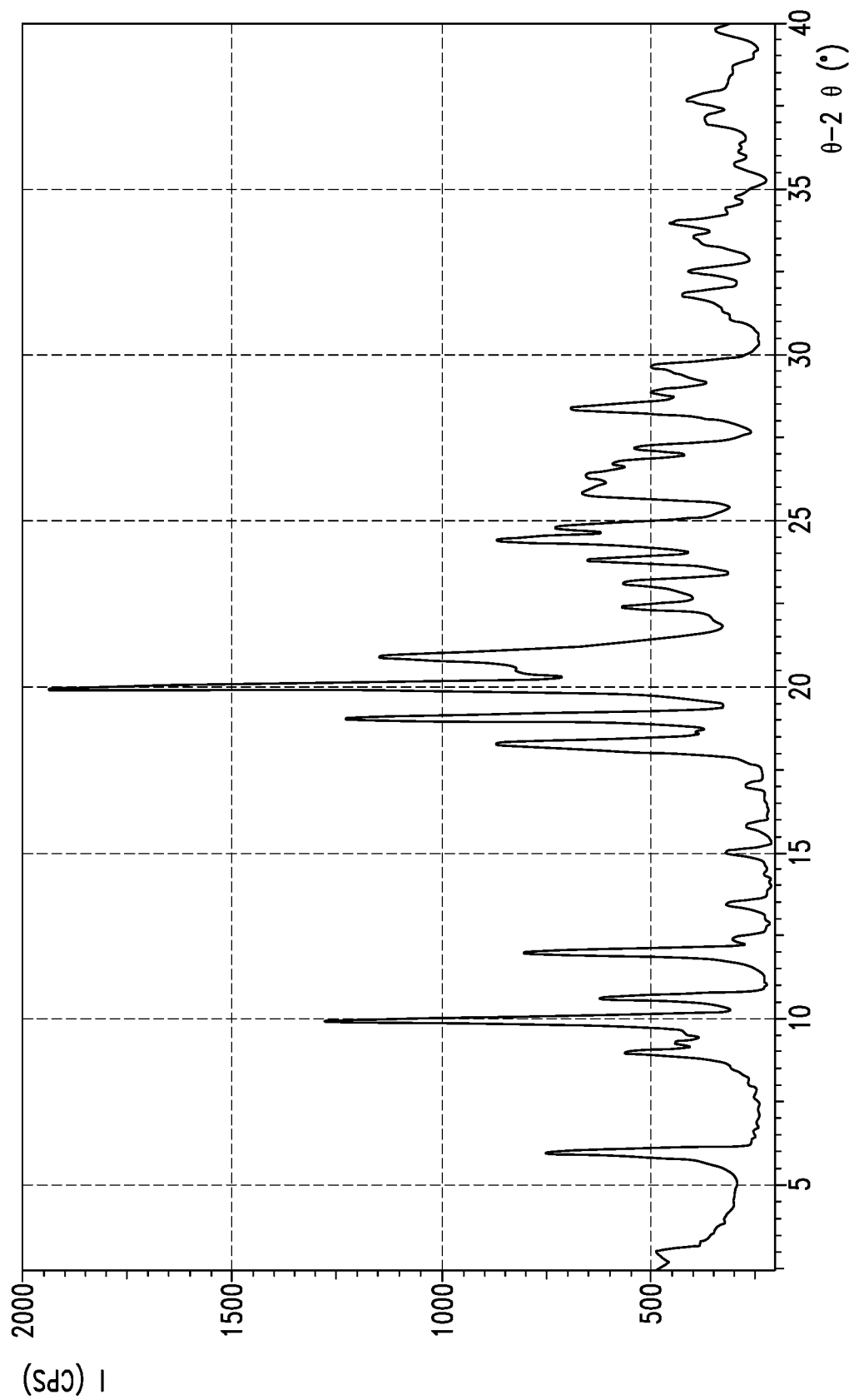
FIG. 1 Powder X-ray diffraction spectrum of crystal form A of compound (I)
FIG. 2 Powder X-ray diffraction spectrum of crystal form B of compound (I)
FIG. 3 Infrared absorption spectrum of crystal form A of compound (I)
FIG. 4 Infrared absorption spectrum of crystal form B of compound (I)
FIG. 5 Solid-state $^{13}$C-NMR spectrum of crystal form A of compound (I)
FIG. 6 Solid-state $^{19}$F-NMR spectrum of crystal form A of compound (I)
FIG. 7 Solid-state $^{15}$N-NMR spectrum of crystal form A of compound (I)

The inventive crystal forms are characterized by their powder X-ray diffraction spectra, infrared absorption spectra, solid-state NMR spectra, or a combination of these means. The powder X-ray diffraction (XRD) spectra, infrared absorption spectra, and solid-state NMR spectra of these crystal forms have unique patterns.

The powder X-ray diffraction spectrum of crystal form A of inventive compound (I) has peaks at diffraction angles 2θ=6.0°, 10.0°, 10.7°, 12.1°, 18.4°, 19.2°, and 20.1°. Also, the powder X-ray diffraction spectrum of crystal form A of inventive compound (I) has the pattern shown in FIG. 1.

The infrared absorption spectrum of crystal form A of inventive compound (I) has absorption peaks at wavenumbers 673 cm$^{-1}$, 810 cm$^{-1}$, 872 cm$^{-1}$, 1010 cm$^{-1}$, 1051 cm$^{-1}$, 1413 cm$^{-1}$, and 1568 cm$^{-1}$. Also, the infrared absorption spectrum of crystal form A of inventive compound (I) has the pattern shown in FIG. 3.

The solid-state $^{13}$C-NMR spectrum of crystal form A of inventive compound (I) has chemical shift peaks at 107.1 ppm, 115.9 ppm, 127.5 ppm, 136.5 ppm, 145.7 ppm, 152.7 ppm, 153.8 ppm, 165.8 ppm, 175.8 ppm, 177.3 ppm, and 179.5 ppm. Also, the solid-state $^{13}$C-NMR spectrum of crystal form A of inventive compound (I) has the pattern shown in FIG. 5.

The solid-state $^{19}$F-NMR spectrum of crystal form A of inventive compound (I) has chemical shift peaks at −77.0 ppm and −72.3 ppm. Also, the solid-state $^{19}$F-NMR spectrum of crystal form A of inventive compound (I) has the pattern shown in FIG. 6.

The solid-state $^{15}$N-NMR spectrum of crystal form A of inventive compound (I) has a chemical shift peak at −347.2 ppm. Also, the solid-state $^{15}$N-NMR spectrum of crystal form A of inventive compound (I) has the pattern shown in FIG. 7.

Furthermore, crystal form A of inventive compound (I) have a melting point of 200° C.

The powder X-ray diffraction spectrum of crystal form B of inventive compound (I) has peaks at diffraction angles 2θ=6.0°, 11.7°, 12.4°, 15.2°, 16.4°, 20.3°, and 22.6°. Also, the powder X-ray diffraction spectrum of crystal form B of inventive compound (I) has the pattern shown in FIG. 2.

The infrared absorption spectrum of crystal form B of inventive compound (I) has absorption peaks at wavenumbers 667 cm$^{-1}$, 803 cm$^{-1}$, 885 cm$^{-1}$, 1012 cm$^{-1}$, 1032 cm$^{-1}$, 1402 cm$^{-1}$, and 1597 cm$^{-1}$. Also, the infrared absorption spectrum of crystal form B of inventive compound (I) has the pattern shown in FIG. 4.

It should be noted that when measurement conditions are good, for example when a high performance measuring instrument is used and the sample is of high purity, other unique peaks in addition to those described above can be found on the powder X-ray diffraction spectra, infrared absorption spectra, and/or solid-state NMR spectra of crystal form A and B of inventive compound (I).

For example, on the powder X-ray diffraction spectrum of crystal form A of inventive compound (I), one or a plurality of peaks at diffraction angles 2θ=9.1°, 21.1°, 24.5°, and 28.4° can also sometimes be observed simultaneously, and on the powder X-ray diffraction spectrum of crystal form B of inventive compound (I), a peak at diffraction angle 2θ=24.4° can also sometimes be observed.

Conversely, when measurement conditions are inadequate, for example with a low purity sample, it is sometimes not possible to observe all of the abovementioned peaks on the powder X-ray diffraction spectra, infrared absorption spectra, and/or solid-state NMR spectra of crystal forms A and B of inventive compound (I). Even in such cases, if the plurality of peaks that can be found are the same as the peak values described above, those skilled in the art can, on overall consideration, sometimes verify that the sample contains crystal form A or B of inventive compound (I). In other words, identification of suspected infringing substance and crystal form A or B of inventive compound (I) depends ultimately on "whether the crystal is the same or not", and this decision is based not on whether all the peaks on the powder X-ray diffraction spectra, infrared absorption spectra or solid-state NMR spectra the are the same, but on whether the overall pattern is the same.

The values of the diffraction angle 2θ peaks on a powder X-ray diffraction spectrum can vary slightly depending on measurement conditions such as the measurement error of the instrument and the condition of the sample being measured and so even if there are small differences in the 2θ values, whether or not the crystal form is the same should be decided by examining the overall pattern of the appropriate spectrum; crystal forms within the error range are included the present invention. The 2θ value error is thought to be ±0.5°. Specifically, for a crystal identified from the abovementioned diffraction angles, within a ±0.5° range is deemed "the same". Though in accordance with the 16$^{th}$ edition of the Japanese Pharmacopoeia, powder X-ray diffraction spectra peaks that are within ±0.2° can be said to be the same, and this can also be deemed common knowledge to those skilled in the art.

For example, a powder X-ray diffraction spectrum obtained under ordinary measurement conditions is said to "have a peak at a diffraction angle 2θ value of 6.0°" if the diffraction angle 2θ value is in the range of from 5.5° to 6.5°, i.e., 6.0±0.5°; however a powder X-ray diffraction spectrum obtained under particularly rigorously controlled measurement conditions is said to "have a peak at a diffraction angle 2θ value of 6.0°" if the diffraction angle 2θ value is in the range of from 5.8° to 6.2°. The same applies to the other peaks.

It should be noted that the measurement values in the following examples are within these error ranges.

Figure 2:
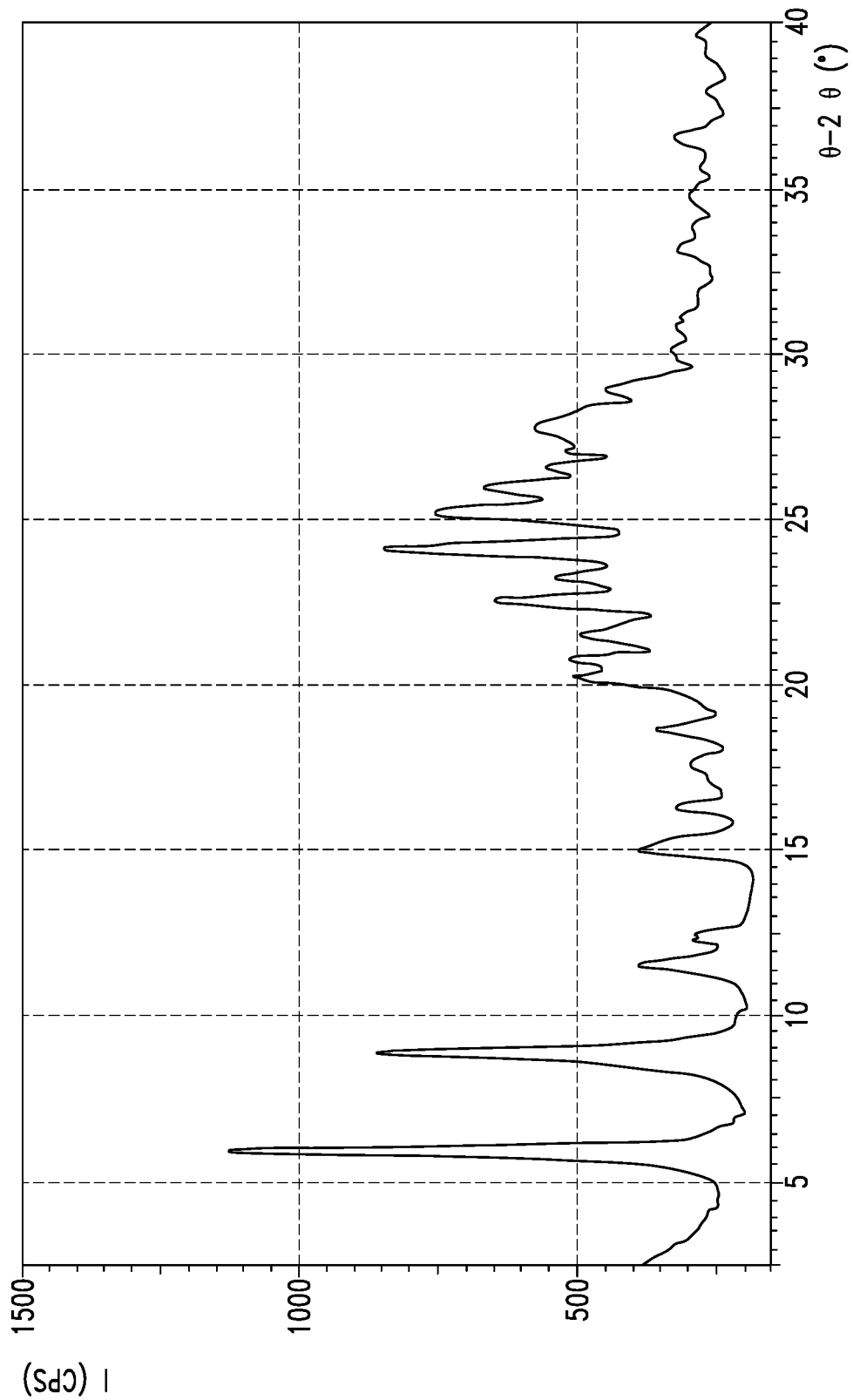

Similarly, the relative intensities at diffraction angles 2θ on powder X-ray diffraction spectra also vary somewhat, in accordance with the error of the measurement instrument used and the effects of low crystallinity due to the size, shape, orientation, and pulverization of the crystal particles in the sample measured; therefore even when the relative intensities of the peaks on the powder X-ray diffraction spectra differ somewhat from those shown in FIG. 1 and FIG. 2, those skilled in the art can, by making an overall judgement of the positions of the peaks, sometimes verify that these are spectra of crystal forms A and B of inventive compound (I).

Figure 3:
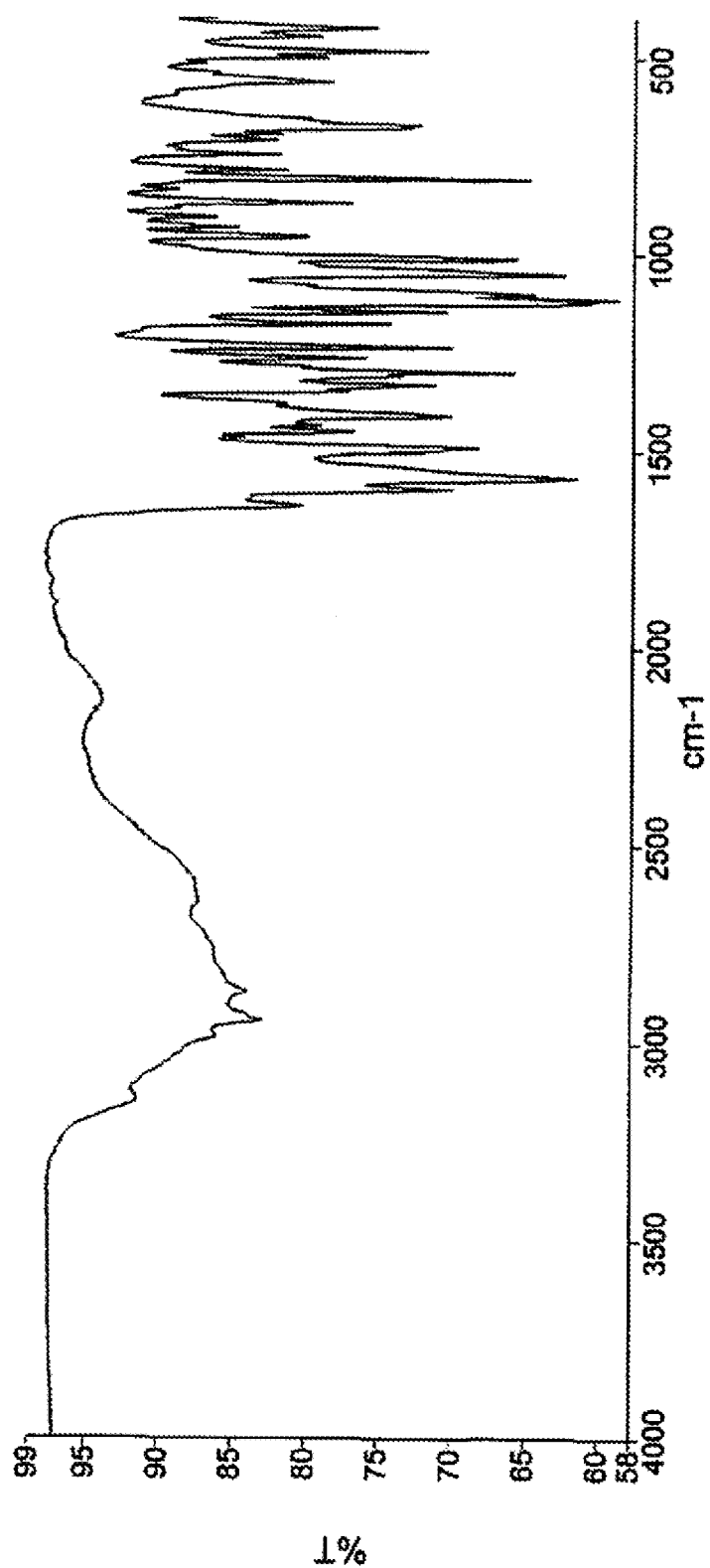
Figure 4:
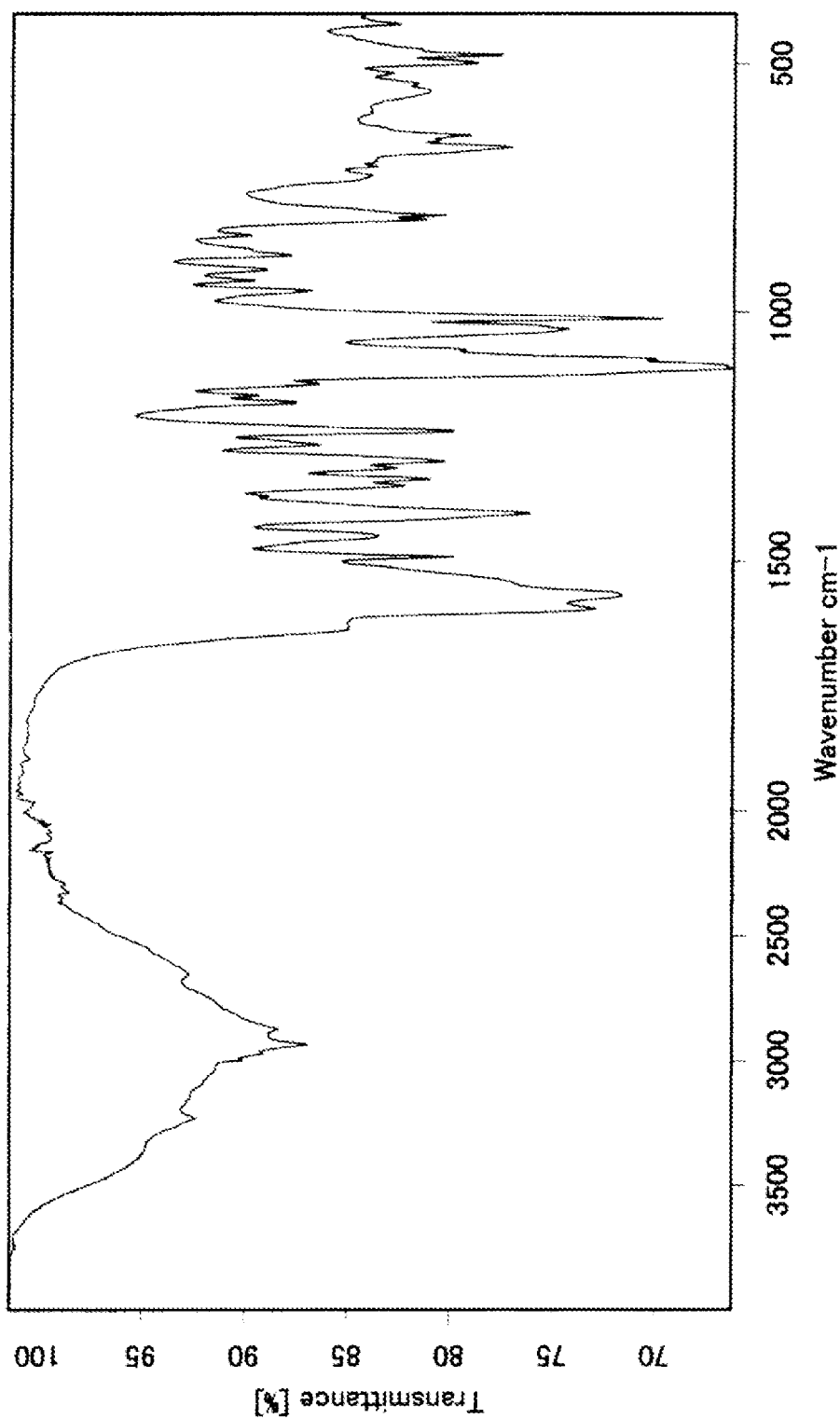

The infrared absorption spectra shown in FIG. 3 and FIG. 4 were measured by the total reflection method (ATR method). Known special features of the total reflection method are that, compared to the transmission method and the diffuse reflectance method (referred to as transmission methods; in these measurement methods the sample is often diluted using KBr powder and then measured), there is usually higher absorption intensity on the low wavenumber side, and the absorption peaks shift from several $cm^{-1}$ to several tens of $cm^{-1}$ to the low wavenumber side. In response to the absorption peak shifts, total reflection-measuring devices are often provided with a function known as "ATR correction", which converts total reflection method measurement results to transmission method measurement results based on more data than is used in the total reflection method and transmission methods. The absorption peak values differ greatly, and so whether the results were obtained with or without "ATR correction" must be noted. The infrared absorption spectra shown in FIG. 3 and FIG. 4 were obtained without "ATR correction".

In infrared absorption spectra, absorption peak errors are common even when the same measurement method is used (even when the total reflection measurement method used is the same in terms of whether or not "ATR correction" is applied). These errors are usually in the range of ±0.5 $cm^{-1}$. Therefore the crystal form identified from the abovementioned wavenumbers includes those that match in the range of ±0.5 $cm^{-1}$.

Errors in the chemical shifts in solid-state NMR spectra are also common. These errors are usually in the range of ±0.5 ppm, and there can be additional ±0.5 ppm errors depending on the condition of the solid-state sample. Therefore the crystal form identified from the abovementioned chemical shifts includes those that match in the range of from ±0.5 ppm to ±1.0 ppm.

[8-Chloro-3-(4-chlorobenzyl)-4-difluoromethoxy-2-ethyl-quinolin-5-yloxy]acetic acid can be produced by the production method described in abovementioned patent citation 1, for example. Compound (I) is obtained, for example, by adding L-lysine to a mixed solution of [8-chloro-3-(4-chlorobenzyl)-4-difluoromethoxy-2-ethyl-quinolin-5-yloxy]acetic acid and solvent.

In this specification, melting point refers to that measured using a differential scanning calorimeter. Generally, a pharmaceutical drug substance needs to be stable at the temperatures and pressures employed during tabletting, and on long-term storage, and so the crystal form must have a high melting point and excellent thermal stability.

The inventive crystal form of compound (I) can be obtained by various production methods; typical examples are shown below.

The crystal form of compound (I) can be obtained by dissolving or suspending compound (I) in solvent, or dissolving or suspending [8-chloro-3-(4-chlorobenzyl)-4-difluoro-methoxy-2-ethylquinolin-5-yloxy]acetic acid and L-lysine in solvent, and then crystallizing by concentration, refrigeration or the addition of a poor solvent.

More specifically, if the solution is unsaturated a solution of compound (I) is obtained, and if the solution is supersaturated the compound may precipitate out directly as crystals or remain in solution, depending on the conditions such as the type, concentration, and temperature of the solvent. Those skilled in the art can select the conditions such as solvent, concentration, and temperature in order to obtain a super-saturated or unsaturated solution, as appropriate. Compound (I) can be precipitated out of solution as crystals by methods such as concentrating or cooling the solution, or adding a poor solvent. Stable crystals can be obtained from suspension as described above and by solvent-mediated transition; that is, using the principle of transition to the most stable form of crystals at that solvent composition and temperature.

Examples of solvents that can be used are N,N-dimethylformamide, N,N-dimethylacetamide, dimethyl sulfoxide, dichloromethane, chloroform, acetonitrile, ethanol, methyl formate, ethyl formate, methyl acetate, ethyl acetate, propyl acetate, isopropyl acetate, butyl acetate, isobutyl acetate, methanol, ethanol, 1-propanol, 2-propanol, 1-butanol, isobutyl alcohol, 2-butanol, t-butyl alcohol, 1-pentanol, 3-methyl-1-butanol, neopentyl alcohol, 2-ethoxymethanol, 2-ethoxyethanol, 2,2,2-trifluorodiethyl ether, 1,1,1,3,3,3-hexafluoro-2-propanol, diisopropyl ether, t-butyl methyl ether, 1,2-dimethoxyethane, tetrahydrofuran, 1,4-dioxane, cyclopentyl methyl ether, anisole, acetone, 2-butanone, 4-methyl-2-pentanone, cyclohexanone, pentane, hexane, heptane, cyclohexane, methylcyclohexane, tetralin, toluene, xylene, water, and mixed solvents comprising two or more selected from these. From an economic perspective and from an industrial perspective, the more preferred solvents are acetonitrile, ethyl acetate, propyl acetate, isopropyl acetate, butyl acetate, methanol, ethanol, 1-propanol, 2-propanol, tetrahydrofuran, 1,4-dioxane, acetone, 2-butanone, hexane, heptane, water, and mixed solvents comprising two or more selected from these.

There are no particular limitations regarding the amount of solvent used, and 5-100×volume is preferred, ≤50×volume is more preferred, and ≤20×volume is even more preferred. Hereafter, 1×volume refers to 1 mL of solvent per 1 g of [8-chloro-3-(4-chlorobenzyl)-4-difluoromethoxy-2-ethylquinolin-5-yloxy]acetic acid or compound (I). Preferred solvents for minimizing the amount of solvent are ethanol, 1-propanol, 2-propanol, tetrahydrofuran, and 1,4-dioxane, which are solvents in which [8-chloro-3-(4-chlorobenzyl)-4-difluoromethoxy-2-ethylquinolin-5-yloxy]acetic acid is highly soluble.

There are no particular limitations regarding the temperature conditions, agitation conditions, or time to filtration after crystallization has started; these conditions affect the yield, chemical purity, particle size, etc., of the crystal form and so it is preferable to set an appropriate combination of conditions in accordance with the target.

When crystallization from solution is performed, is it effective to add seed crystals of the same crystal form as the target crystal form. The amount thereof is usually from around 0.01% by weight to 20% by weight, preferably 0.1% by weight to 10% by weight, of the drug substance [8-chloro-3-(4-chlorobenzyl)-4-difluoromethoxy-2-ethylquinolin-5-yloxy]acetic acid or compound (I), and it is preferably already pulverized. At the time of addition, the crystals to be obtained are preferably in the region of super-saturation; it is not necessary for them to be already super-saturated at the time of addition, but it is important that the system is such that the added crystals do not all dissolve.

The inventive crystal form A of compound (I) is relatively easy to obtain, and can be crystallized by the production methods described above under a wide range of conditions (combinations of various solvents). The crystals obtained from the resulting suspension are filtered and dried to obtain crystal form A. The filtration can be performed by a common method; examples of methods that can be used are natural filtration, filtration under increased pressure, filtration under reduced pressure, and centrifugation. The drying can be performed by a common method; examples of methods that can be used are natural drying, drying under reduced pressure, heated drying, and heated drying under reduced pressure.

Inventive crystal form B of compound (I) is a hydrate crystal form, and can be obtained using a combination of solvents that includes water. Alcohols such as ethanol and 2-propanol are preferred as the solvent used in combination with water. For example, the crystal form can be obtained by dissolving compound (I) in a mixed solvent containing ethanol and water at a ratio of 1:1 (80×volume), concentrating and then drying. The drying can comprise natural drying, drying under reduced pressure, heated drying, or heated drying under reduced pressure. In heated drying under reduced pressure it is confirmed that no water of crystallization is lost even at 80° C., but at higher temperatures caution is required.

The inventive crystal form of compound (I) can be used as the active ingredient in pharmaceuticals. It is also possible to use not only a single crystal, but also mixtures of two or more crystal forms.

The inventive crystal form of compound (I) is advantageous in terms of ease of handling during production, reproducibility, stability, storage stability, etc., compared to when non-crystalline.

Also, the inventive crystal form of compound (I) is a L-lysine salt in crystal form, and has better storage stability than crystals of the free form.

The inventive crystal form of compound (I) can be used to obtain pharmaceutical compositions using pharmaceutically acceptable carrier.

Formulations containing inventive crystal form of compound (I) are prepared using additives commonly used in formulation preparation. Examples of these additives for solid formulations include excipients such as lactose, white sugar, glucose, corn starch, potato starch, crystalline cellulose, light anhydrous silicic acid, synthetic aluminum silicate, magnesium metasilicate aluminate, and calcium hydrogen phosphate; binders such as crystalline cellulose, carboxymethyl cellulose, hydroxypropyl cellulose, carboxymethyl-cellulose sodium and polyvinylpyrrolidone; disintegrating agents such as starch, carboxymethyl-cellulose sodium, carboxymethylcellulose calcium, croscarmellose sodium, and carboxymethylstarch sodium; lubricants such as talc and stearates; coatings such as hydroxymethyl-propyl cellulose, hydroxypropyl methyl cellulose phthalate, and ethyl cellulose; and colorants. For semi-solid formulations, they include base such as white vaseline; and for liquid formulations they include solvents such as ethanol; solubilizing agents such as ethanol; preservatives such as para-oxybenzoic acid esters; isotonizing agents such as glucose; buffers such as citrates; antioxidants such as L-ascorbates; chelating agents such as EDTA; and suspending agents and emulsifiers such as polysorbate 80.

The inventive crystal form of compound (I) can be used in any dosage form, such as solid formulations, semi-solid formulations and liquid formulations, and in any appropriate oral or non-oral formulation (injection agent, transdermal agent, eyedrops, suppository, nasal agent, inhalant, etc.).

Pharmaceutical compositions containing inventive crystal form of compound (I) as active ingredient can be used as drugs for the treatment or prevention of diseases in which CRTH2 receptors participate, such as bronchial asthma, chronic obstructive pulmonary disease, bronchitis, cystic fibrosis, perennial allergic rhinitis, seasonal allergic rhinitis, chronic eosinophilic rhinosinusitis, chronic noneosinophilic rhinosinusitis, psoriasis, atopic and nonatopic dermatitis, chronic spontaneous urticaria, Crohn's disease, ulcerative colitis, eosinophilic gastrointestinal disease, and irritable bowel disease. Here, "prevention" refers to the prevention of disease or symptoms in an individual who does not yet exhibit disease or symptoms, and "treatment" refers to affecting cure, inhibition or improvement of disease or symptoms in an individual who already exhibits disease or symptoms.

EXAMPLES

Powder X-Ray Diffraction Measurement Method
The powder X-ray diffraction of the inventive crystal form was measured under the following conditions.
Measurement instrument: Shimadzu Corporation
Measurement conditions: Source Cu-Kα, 40 kV-40 mA, scan 5-40°, scan time 35 seconds
Infrared Absorption Measurement Method
The infrared absorption spectrum of the inventive crystal form was measured under the following conditions in accordance with the ATR infrared absorption spectra measurement method described in the common test methods section of the Japanese Pharmacopoeia.
Conditions 1
Measurement instrument: Perkin Elmer Spectrum Two
Measurement conditions: 4000-400 $cm^{-1}$, resolution 4 $cm^{-1}$, accumulation 64 times
Conditions 2
Measurement instrument: Bruker-Optics Alpha
Measurement conditions: 4000-400 $cm^{-1}$, resolution 4 $cm^{-1}$, accumulation 24 times
Solid-State $^{13}$C-NMR Measurement Method
The solid-state $^{13}$C-NMR of the inventive crystal form was measured under the following conditions.
Measurement instrument: Bruker Avance III HD400
Measurement conditions: Pulse mode CP/MAS measurement, pulse repeat time 20 seconds, chemical shift standard hexamethylbenzene (external standard: 17.35 ppm)
Solid-State $^{19}$F-NMR Measurement Method
The solid-state $^{19}$F-NMR of the inventive crystal form was measured under the following conditions.
Measurement instrument: Bruker Avance III HD400
Measurement conditions: Pulse mode CP/MAS measurement, pulse repeat time 55 seconds, chemical shift standard hexafluorobenzene (external standard: −163.0 ppm)

Solid-State $^{15}$N-NMR Measurement Method

The solid-state $^{15}$N-NMR of the inventive crystal form was measured under the following conditions.

Measurement instrument: Bruker Avance 400

Measurement conditions: Pulse mode CP/MAS measurement, pulse repeat time 15 seconds, chemical shift standard ammonium chloride (external standard: −341.2 ppm)

Melting Point Measurement Method

The melting point of the inventive crystal form was measured under the following conditions.

Measurement instrument: TA Instruments Japan Q2000

Measurement conditions: Measurement range 30-320° C., temperature elevation rate 20° C./minute, on set value Solution NMR Measurement Method The measured solution $^1$H-NMR spectrum (400 mHz, DMSO-$d_6$ or CDCl$_3$) shows the chemical shifts (δ: ppm) and coupling constants (J: Hz). The symbols used below are as follows.

s=singlet, d=doublet, t=triplet, q=quartet, brs=broad singlet, m=multiplet

Measurement instrument: Bruker BioSpin AV-400M

Example 1

Production of [8-chloro-3-(4-chlorobenzyl)-4-difluoro-methoxy-2-ethylquinolin-5-yloxy]acetic Acid L-Lysine Salt in Crystal Form A 8.0 g of [8-chloro-3-(4-chlorobenzyl)-4-difluoromethoxy-2-ethylquinolin-5-yloxy]acetic acid were dissolved in 96 mL of 2-propanol at 45° C., 24 mL of an aqueous solution of 2.6 g L-lysine were added, and the system was agitated at 45° C. for 1 hour. It was then cooled to 15° C. over a period of 2 hours, and then crystals were obtained by filtration and washed using 24 mL of 2-propanol. The crystals were dried under reduced pressure at 40° C. to obtain 9.0 g of [8-chloro-3-(4-chlorobenzyl)-4-difluoromethoxy-2-ethylquinolin-5-yloxy]acetic acid L-lysine salt in crystal form. The powder XRD of the resulting crystal form is shown in FIG. 1. Peaks were observed at diffraction angles 2θ=6.0°, 10.0°, 10.7°, 12.1°, 18.4°, 19.2°, and 20.1°. The infrared spectrum of the resulting crystal form under conditions 1 is shown in FIG. 3. Peaks were observed at wavenumbers 673 cm$^{-1}$, 810 cm$^{-1}$, 872 cm$^{-1}$, 1010 cm$^{-1}$, 1051 cm$^{-1}$, 1413 cm$^{-1}$, and 1568 cm$^{-1}$.

Figure 5:
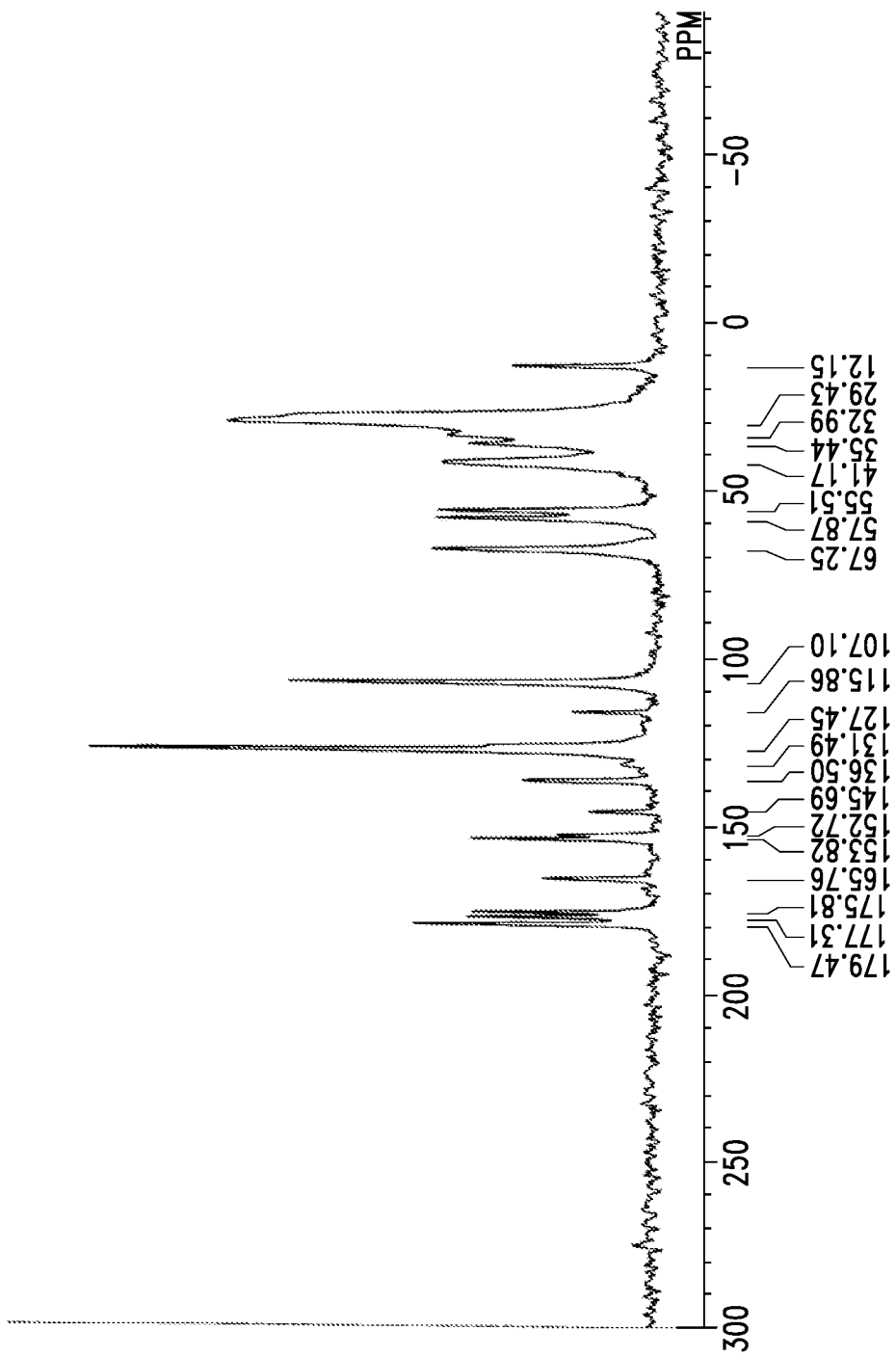

The solid-state $^{13}$C-NMR spectrum of the resulting crystal form is shown in FIG. 5. Chemical shift peaks were observed at 107.1 ppm, 115.9 ppm, 127.5 ppm, 136.5 ppm, 145.7 ppm, 152.7 ppm, 153.8 ppm, 165.8 ppm, 175.8 ppm, 177.3 ppm, and 179.5 ppm.

Figure 6:
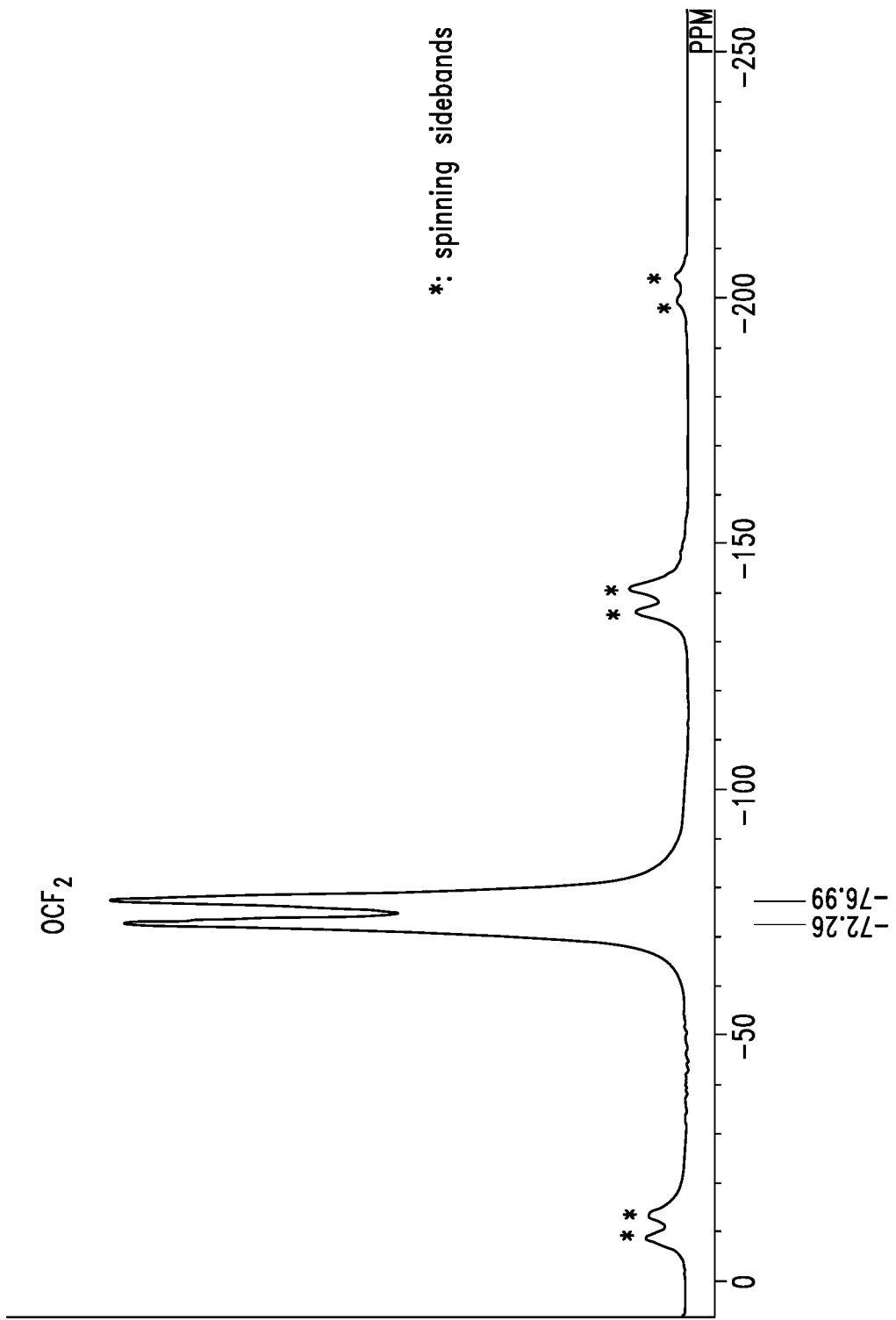

The solid-state $^{19}$F-NMR spectrum of the resulting crystal form is shown in FIG. 6. Chemical shift peaks were observed at −77.0 ppm and −72.3 ppm.

Figure 7:
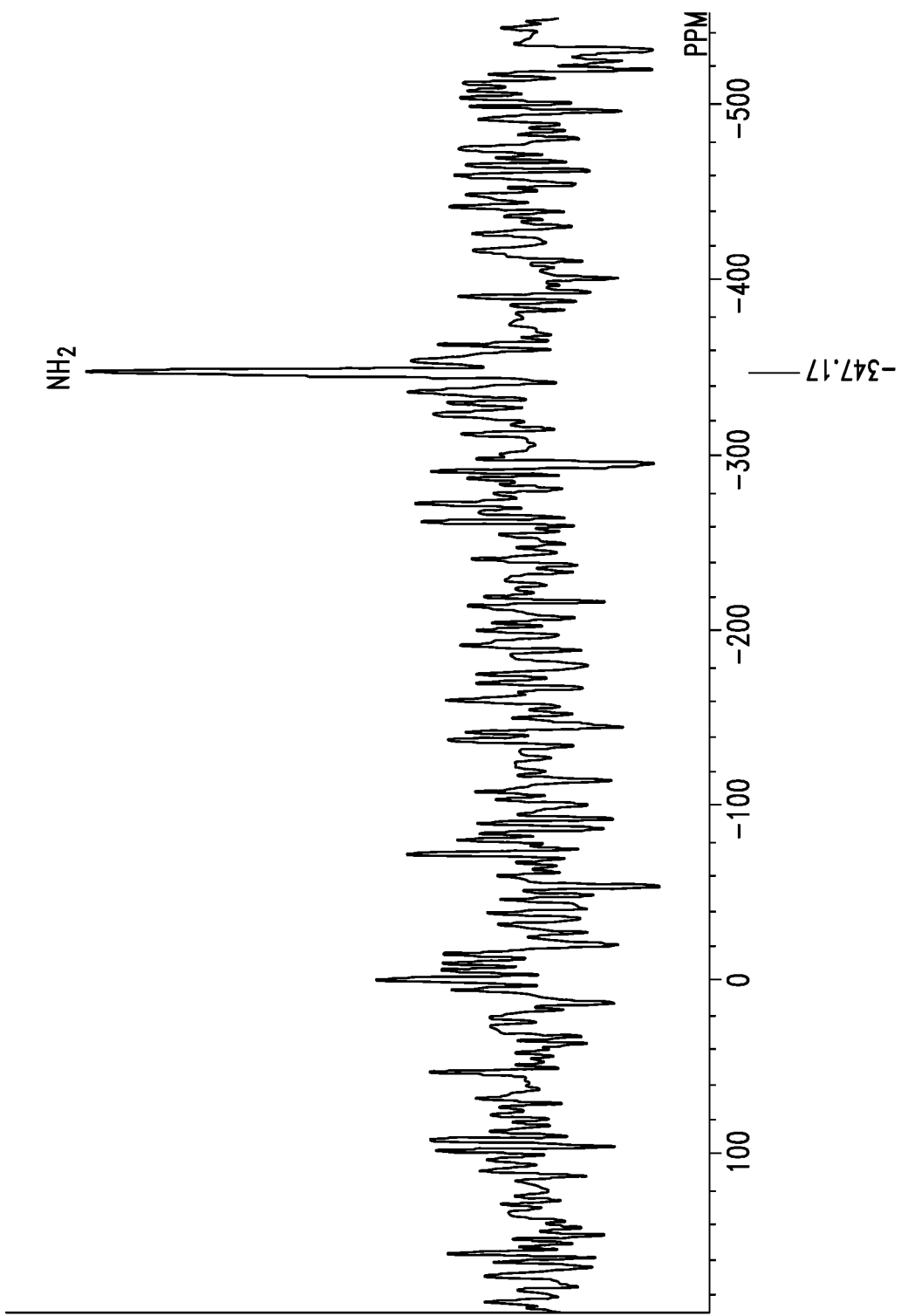

The solid-state $^{15}$N-NMR spectrum of the resulting crystal form is shown in FIG. 7. A chemical shift peak was observed at −347.2 ppm.

The melting point was 200° C.

Solution $^1$H-NMR (400 MHz, DMSO-$d_6$) δ: 1.21 (3H, t, J=7.4 Hz), 1.25-1.75 (6H, m), 2.73 (2H, t, J=7.2 Hz), 2.83 (2H, q, J=7.3 Hz), 3.17 (1H, t, J=6.0 Hz), 4.32 (2H, s), 4.46 (2H, s), 6.89 (1H, d, J=8.8 Hz), 7.12 (1H, d, J=8.8 Hz), 7.33 (1H, d, J=8.8 Hz), 7.81 (1H, d, J=8.8 Hz)

Example 2

Production of [8-chloro-3-(4-chlorobenzyl)-4-difluoro-methoxy-2-ethylquinolin-5-yloxy]acetic Acid L-Lysine Salt in Crystal Form B 4.8 g of crystal form A of compound (I) were dissolved at room temperature in 420 mL of an ethanol/water=1/1 mixed solution, and concentrated under reduced pressure at 40° C. The resulting concentrate was dried under reduced pressure at 65° C. to obtain 4.8 g of [8-chloro-3-(4-chlorobenzyl)-4-difluoromethoxy-2-ethylquinolin-5-yloxy]acetic acid L-lysine salt in crystal form. The powder XRD of the resulting crystal form is shown in FIG. 2. Peaks were observed at diffraction angles 2θ=6.0°, 11.7°, 12.4°, 15.2°, 16.4°, 20.3°, and 22.6°. The infrared spectrum of the resulting crystal form under conditions 2 is shown in FIG. 4. Peaks were observed at wavenumbers 667 cm$^{-1}$, 803 cm$^{-1}$, 885 cm$^{-1}$, 1012 cm$^{-1}$, 1032 cm$^{-1}$, 1402 cm$^{-1}$, and 1597 cm$^{-1}$.

Solution $^1$H-NMR (400 MHz, DMSO-$d_6$) δ: 1.21 (3H, t, J=7.4 Hz), 1.25-1.75 (6H, m), 2.73 (2H, t, J=7.2 Hz), 2.83 (2H, q, J=7.3 Hz), 3.22 (1H, t, J=6.0 Hz), 4.32 (2H, s), 4.50 (2H, s), 6.90 (1H, d, J=8.8 Hz), 7.11 (1H, d, J=8.4 Hz), 7.33 (1H, d, J=8.4 Hz), 7.80 (1H, d, J=8.4 Hz)

Comparative Example 1

Production of Free-Form Crystals of [8-chloro-3-(4-chlorobenzyl)-4-difluoromethoxy-2-ethylquinolin-5-yloxy]acetic Acid An aqueous solution obtained by dissolving sodium hydroxide (14 g) in water (350 mL) was added to a methanol (2000 mL) solution of [8-chloro-3-(4-chlorobenzyl)-4-difluoromethoxy-2-ethylquinolin-5-yloxy]acetic acid ethyl ester (100 g) obtained in accordance with the method described in example 39, preparation 39c of international patent publication WO2007/036743, and the resulting system was agitated at 35° C. for 1 hour. It was then cooled to room temperature, 2000 mL of water were added with agitation, and the pH was adjusted to 4 using dilute hydrochloric acid and aqueous sodium hydroxide solution. The precipitated crystals were filtered and then dried under reduced pressure at 42° C. to obtain 95 g of free-form crystals of [8-chloro-3-(4-chlorobenzyl)-4-difluoromethoxy-2-ethylquinolin-5-yloxy]acetic acid. The resulting crystals had a melting point of 141° C.

Example 3

The storage stability of the compound (I) crystal form A obtained in example 1 was compared with that of the free-form crystals obtained in comparative example 1.

The respective crystals were introduced into a glass vessel which was then tightly sealed and stored at 40° C., relative humidity 75° C. for 3 months; the amount of related substances before and after storage was measured by liquid chromatography; the results are shown in Table 1. The values are the total amount of related substances, which are produced impurities, as measured to ≥0.03%.

TABLE 1

|  | At the start | After 3 months |
|---|---|---|
| Compound (I) crystal form A | 0.53% | 0.59% |
| Free-form crystals | 1.37% | 1.95% |

Compound (I) crystal form A exhibited better storage stability than the free-form crystals.

INDUSTRIAL APPLICABILITY

The inventive crystal form of compound (I) can be used for the production of pharmaceutical products.

The invention claimed is:

1. A crystal form of 8-chloro-3-(4-chlorobenzyl)-4-difluoro-methoxy-2-ethylquinolin-5-yloxy]acetic acid L-lysine salt having a melting point of 200° C.

2. A crystal form of 8-chloro-3-(4-chlorobenzyl)-4-difluoro-methoxy-2-ethylquinolin-5-yloxy]acetic acid L-lysine salt having a X-ray powder diffraction (XRPD) spectrum comprising peaks with the following diffraction angles (2θ±0.5°): 6.0°, 10.0°, 10.7°, 12.1°, 18.4°, 19.2°, and 20.1°.

3. The crystal form of claim 2, wherein the XRPD spectrum further comprises peaks with the following diffraction angles (2θ±0.5°): 9.1°, 21.1°, 24.5°, and 28.4°.

4. The crystal form of claim 2 having a X-ray powder diffraction (XRPD) spectrum comprising peaks with the following diffraction angles (2θ±0.2°): 6.0°, 10.0°, 10.7°, 12.1°, 18.4°, 19.2°, and 20.1°.

5. The crystal form of claim 4, wherein the XRPD spectrum further comprises peaks with the following diffraction angles (2θ±0.2°): 9.1°, 21.1°, 24.5°, and 28.4°.

6. The crystal form of claim 2 having a X-ray powder diffraction spectrum as shown in FIG. 1 (2θ±0.5°).

7. A crystal form of 8-chloro-3-(4-chlorobenzyl)-4-difluoro-methoxy-2-ethylquinolin-5-yloxy]acetic acid L-lysine salt having an infrared absorption spectrum, as measured by attenuated total reflection (ATR), with absorption peaks at the following wavenumbers (±0.5 cm$^{-1}$): 673 cm$^{-1}$, 810 cm$^{-1}$, 872 cm$^{-1}$, 1010 cm$^{-1}$, 1051 cm$^{-1}$, 1413 cm$^{-1}$, and 1568 cm$^{-1}$, wherein said wavenumbers are without ATR correction.

8. The crystal form of claim 7 having an infrared absorption spectrum, as measured by attenuated total reflection (ATR), with absorption peaks as shown in FIG. 3, wherein said spectrum is without ATR correction.

9. A crystal form of 8-chloro-3-(4-chlorobenzyl)-4-difluoro-methoxy-2-ethylquinolin-5-yloxy]acetic acid L-lysine salt having a solid state $^{13}$C-NMR spectrum with the following chemical shift peaks (±1.0 ppm): 107.1 ppm, 115.9 ppm, 127.5 ppm, 136.5 ppm, 145.7 ppm, 152.7 ppm, 153.8 ppm, 165.8 ppm, 175.8 ppm, 177.3 ppm, and 179.5 ppm.

10. The crystal form of claim 9 having a solid state $^{13}$C-NMR spectrum with the following chemical shift peaks (±0.5 ppm): 107.1 ppm, 115.9 ppm, 127.5 ppm, 136.5 ppm, 145.7 ppm, 152.7 ppm, 153.8 ppm, 165.8 ppm, 175.8 ppm, 177.3 ppm, and 179.5 ppm.

11. The crystal form of claim 9 having a solid state $^{13}$C-NMR spectrum as shown in FIG. 5 (±1.0 ppm).

12. The crystal form of claim 9 further having a solid-state $^{19}$F-NMR spectrum with the following chemical shift peaks (±1.0 ppm): −77.0 ppm, and −72.3 ppm.

13. The crystal form of claim 9 further having a solid-state $^{19}$F-NMR spectrum with the following chemical shift peaks (±0.5 ppm): −77.0 ppm, and −72.3 ppm.

14. The crystal form of claim 9 further having a solid state $^{19}$F-NMR spectrum as shown in FIG. 6 (±1.0 ppm).

15. The crystal form of claim 9 further having a solid-state $^{15}$N-NMR spectrum with a chemical shift peak (±1.0 ppm) at −347.2 ppm.

16. The crystal form of claim 9 further having a solid-state $^{15}$N-NMR spectrum with a chemical shift peak (±0.5 ppm) at −347.2 ppm.

17. The crystal form of claim 9 further having a solid state $^{15}$N-NMR spectrum as shown in FIG. 7 (±1.0 ppm).

* * * * *